US007857745B2

(12) United States Patent
Delaperriere

(10) Patent No.: US 7,857,745 B2
(45) Date of Patent: Dec. 28, 2010

(54) METHOD FOR FUNCTION MONITORING IN MEDICAL ACCELERATOR SYSTEMS

(75) Inventor: Marc Delaperriere, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1261 days.

(21) Appl. No.: 11/435,449

(22) Filed: May 16, 2006

(65) Prior Publication Data

US 2006/0273746 A1 Dec. 7, 2006

Related U.S. Application Data

(60) Provisional application No. 60/682,534, filed on May 19, 2005.

(30) Foreign Application Priority Data

May 19, 2005 (DE) ........................ 10 2005 023 166

(51) Int. Cl.
*A61N 5/00* (2006.01)

(52) U.S. Cl. ........................................................ 600/1

(58) Field of Classification Search ................. 600/1–2; 315/501; 375/130–132; 250/252.1, 336.1, 250/370.01, 370.09, 370.1, 393, 398, 492.1–492.3, 250/493.1

See application file for complete search history.

(56) References Cited

U.S. PATENT DOCUMENTS

| | | | | |
|---|---|---|---|---|
| 5,214,788 | A * | 5/1993 | Delaperriere et al. | 375/132 |
| 5,895,926 | A * | 4/1999 | Britton et al. | 250/492.3 |
| 6,212,256 | B1 * | 4/2001 | Miesbauer et al. | 378/118 |
| 6,472,834 | B2 * | 10/2002 | Hiramoto et al. | 315/501 |
| 6,498,444 | B1 * | 12/2002 | Hanna et al. | 315/500 |
| 6,677,597 | B1 | 1/2004 | Haberer et al. | |
| 6,714,620 | B2 * | 3/2004 | Caflisch et al. | 378/65 |
| 6,844,689 | B1 * | 1/2005 | Brown et al. | 315/505 |
| 2005/0094768 | A1 * | 5/2005 | Ghelmansarai et al. | 378/108 |

FOREIGN PATENT DOCUMENTS

| | | |
|---|---|---|
| EP | 1 045 399 A1 | 10/2000 |
| EP | 1 454 656 A2 | 9/2004 |

OTHER PUBLICATIONS

European Organization for Nuclear Research (CERN); "Proton-Ion Medical Machine Study (PIMMS) Part II"; Teil, II, S. 171-175, Genf; Aug. 2000.

Brand H. et al. "Therapy Slow Control System, Data Analysis and Online Monitoring," Jehresbericht der Gesellschaft für Schwerionenforschung (GSI), 1997.

German Office Action with English Translation.

* cited by examiner

*Primary Examiner*—Samuel G Gilbert
(74) *Attorney, Agent, or Firm*—Brinks, Hofer, Gilson & Lione

(57) ABSTRACT

A method for function monitoring in medical accelerator systems, wherein at least one signal characterizing the operation of at least one medical accelerator, is acquired, digitized and deposited in digitized form in a data processing system to hold it for evaluation of the accelerator system.

23 Claims, 4 Drawing Sheets

1
2
3
4
N
5
6
7
8
T
9

METHOD FOR FUNCTION MONITORING IN MEDICAL ACCELERATOR SYSTEMS

RELATED APPLICATIONS

The present patent document claims the benefit of the filing date under 35 U.S.C. §119(e) of Provisional U.S. Patent Application Ser. No. 60/682,534, filed May 19, 2005, which is hereby incorporated by reference.

BACKGROUND

1. Field

A method for function monitoring in medical accelerator systems is provided.

2. Related Art

Accelerator systems that generate high-energy electromagnetic radiation or particle radiation are used in medicine for radiation therapy. Radiation therapy exposes regions of a patient's body to the radiation. Energy is transmitted to these exposed regions in order to bring about changes in cell components. Radiation therapy is used particularly in treating cancer by killing tumor cells or reducing the capability of the cells to divide. Both linear and cyclic accelerators can be used in accelerator systems.

Conventionally, it has been necessary to manually connect an oscilloscope to a box in the control room of the accelerator system. This connection enables a user to monitor the signals from the accelerator system relevant for the operation. A proper connection requires time-consuming tuning of the oscilloscope. In addition, the signal information obtained by the oscilloscope must be separately recorded, for example, on paper.

Since the information obtained must be recorded separately, only a small portion of the signal data, for example the amplitude and width, can be picked up or acquired. Generally, this data acquisition is done only at relatively long maintenance intervals, for example, every three months.

Even with arrangements for transmitting the signals received to a servicing device by modem, intervention by the user is still required. The user must still connect the oscilloscope and forward the data. Data acquisition is limited to the brief times in which an oscilloscope is connected. Because of the difficulty of connecting the oscilloscope and tuning the signal, data acquisition generally only takes place when the accelerator system malfunctions or during routine maintenance at certain relatively long maintenance intervals. Thus, monitoring the accelerator system during the operation of the system is hardly possible because the presence of a system technician in the operation room could bother the medical personnel who are operating the system.

Thus, a method that permits improved function monitoring in medical accelerator systems is desired.

SUMMARY

A method for function monitoring in medical accelerator systems is provided. At least one signal that is relevant to the operation of at least one medical accelerator system is picked up or acquired and digitized. The signal is then deposited in digitized form in a data processing system. The data processing system stores the signal for subsequent computer-supported evaluation. The evaluation checks the functionality of the accelerator system.

One or more signals that are relevant for the operation of one or more medical accelerators in a system are acquired. This signal acquisition can be done at any time, including during a treatment operation and/or in the absence of a technician. Based on the signals, quantitative and qualitative properties indicating the quality of operation of the accelerator can be monitored. Signals that are obtained from various components of an accelerator provide information on whether the operating state of the component is considered good, average, or poor.

The signal or signals are initially acquired in analog form. The signal or signals are then digitized. The signal is digitized in order to make use of the capabilities of electronic data processing.

The digitized or electronically readable signal is deposited in a data processing system. This signal is stored in the data processing system for a short-term, for function monitoring close to that time, or for a longer time, to hold for a later computer-controlled evaluation.

In one example embodiment, a function check can be performed in such a way that the digitized signals are called up by one or more technicians and evaluated for special features. The technician can look at signal properties and compare the properties with the properties of signals that are familiar to him, which characterize proper or defective operation.

The acquisition and storage of system signals does not require the intervention by a technician due to automated acquisition. The acquisition can be done at predetermined maintenance intervals or during the use of the medical accelerator. Thus, better quality and more-precise function monitoring becomes possible.

In the data processing system, the amplitude, width, envelope curve, and/or form of the at least one signal is evaluated. In addition to a technician evaluating the signals, a data processing system may also evaluate the digital signal. The data processing system may use a program for monitoring the accelerator system. This evaluation can be programmed to run at certain time intervals or after new data have been input. This evaluation can also be completed whenever a user explicitly starts a program for the evaluation or makes certain inputs into the data processor.

Many signal properties, for example, the amplitude, width, form, and envelope curve, may be used to evaluate the characteristics of the operation of the accelerator. For example, signal amplitude that is small in comparison with normal operation signal amplitude can be an indication of a low number of particles in the accelerator, while an envelope curve that is altered in its parameters or even in its basic form is an indication of instabilities, synchronization problems, triggering problems, or the like. Thus, the data processing system can perform the evaluation act. Accordingly, there is less work for technicians, or their presence on-site is not absolutely necessary because no further intervention may be needed to evaluate the signals.

The at least one signal relevant to the operation of the accelerator can be evaluated in the data processing system as a function of predetermined rules and/or as a function of a comparison with at least one further picked up and/or predetermined reference signal. The data processing system has a set of rules stored in memory that is available for use in a database, in the form of an expert system, or the like. Certain rules in terms of the signal curve for one or more certain signals are stored, for instance with a view to the amplitude or the signal length, and the rules can be constructed hierarchically. In such a hierarchical construction, a basic construction or a basic error is first detected based on a certain rule, and fine analysis is thereupon done by executing a subordinate set of rules. The rules may be specified to the user or added to by a user.

When considering the individual properties of the particular accelerator or accelerators of the accelerator system, access to reference signals may be advantageous. These reference signals may have been picked up separately with the accelerator system or may be characteristic of the operation of a certain type of accelerator. The reference signals serve as reference signals for error-free operation or also for operation with certain errors that have already occurred earlier with this accelerator or in general with accelerators of that type. A comparison with one or more reference signals can be done in multiple steps, depending on what deviations from a reference signal serving as a basic signal have been detected.

During the evaluation of the signal in the data processing system, a prognosis is made in terms of the operating state of the accelerator. For example, the typical operation times of accelerators of a comparable or a same type, and/or the service life that is expected for error-free operation, can be displayed. Signals that indicate wear or undesired operation characteristics can also be displayed. For example, the screen can display how long the accelerator can be expected to continue to be used before replacement of the applicable components is necessary if there are changes in the klystron impedance.

The outcome of the evaluation can be deposited in the data processing system for a predetermined length of time. The length of time can be defined by a user. The outcome of the evaluation is created, for example, in text form, graphic form, or in a combination of text and graphic elements. The outcome can be stored in memory until a certain number of further signals has been picked up and correspondingly new outcomes of evaluation have been obtained. The number of outcomes stored in memory or certain outcomes to be eliminated can be defined by a user of the data processing system. This can be done by way of an input in a program for signal evaluation. The outcomes can also be deleted after a certain problem has been solved or an error has been eliminated. Outcomes may be deposited for an indefinite time. Manual deletion can be done in the event of scarce memory resources.

The at least one characterizing signal can be deposited in the data processing system for a predetermined length of time and/or a length of time that can be defined by a user. For example, not only the outcomes of evaluation but also the characterizing signals acquired can be archived for a defined time interval, as a function of newly acquired signals, or as a function of the elimination of existing problems. The signals may be chronologically organized, such that signals are present for not only the instant of acquisition, and outcomes of evaluation are present not only directly after the assessment of the signals, but they remain accessible for longer periods of time.

It is possible to recognize trends in the signal course or in the outcomes of evaluation because of the archive. For example, a gradual worsening of the system may be recognized after evaluation of the archived signals. The time dependency of the function monitoring uses archived signals because archived signals can be called up without problems at a later time and evaluated by the data processing system or manually. The "lifetime" of these data in the archive can be adapted to the requirements of maintenance or of maintenance personnel. The archive offers the advantage that the stored signals can be accessed from automatic routines and from remote locations, independent of time. For example, service personnel of the accelerator or the manufacturer may be interested in accessing the signals from a remote location.

The relevant accelerator signal can be picked up as a function of acquisition specifications. More specifically, the signal can be acquired continuously, at certain times, at certain time intervals, as a function of at least one trigger signal, and/or multiple times. In continuous signal acquisition, a memory overflow must be prevented. By deleting older signals, it is assured that for maintenance purposes or in the event that errors occur, all the important signals characterizing the operation can always be called up. The signal acquisition can also be done at certain times, for instance every day at the same time, or once a week or once a month. Acquisition at certain time intervals is also possible, either in accordance with the previous maintenance intervals or optionally more often, so that a larger and thus more-conclusive amount of data can be accessed.

It is useful to acquire a signal multiple times. After acquiring a signal multiple times reference signals of the accelerator, or signals that reflect the course of the occurrence of a malfunction, will be available for comparison by the data processing system or by the service technician. Triggering events can also be useful. In the event of an interlock or shutoff of one accelerator, for example, it is useful to acquire the signals that characterize the operation. Thus, the cause of the error can be analyzed. A triggering event can also be made as a function of the phases of operation of the accelerator, for example, in the radiation phase or in the ramp-up or ramp-down phase. More specifically, status-based maintenance can be implemented using trigger times or as a function of triggered time stamps.

It is advantageous to acquire different characterizing signals, and in particular, all the accessible characterizing signals. For status-based maintenance or function monitoring, at least nearly all the characterizing signals may be ascertained. For a typical linear accelerator in cancer research, for example, a number equal to or less than ten signals can be named.

Signals can be picked up from a plurality of accelerators. Generally, accelerator systems in a system include two, three, or more accelerators of the same or different types, depending on the specialization of the particular medical facility. It is also possible to acquire signals from accelerators in different medical facilities in association with each other, or from accelerators that are associated with a service association. This makes it possible to evaluate other user's qualified data for comparison of the signal. This makes integration in terms of location easily possible.

Acquired signals from a plurality of accelerators, in particular accelerators that are structurally identical and/or similar, can be compared with one another. Thus, in structurally similar accelerators, it can be decided which type is optionally more suitable for a particular application. For example, by comparing signals from structurally identical accelerators that indicate wear, it can be ascertained how the operation of the accelerators should be optimized, or what grounds might be responsible for an operation that is more vulnerable to error. Even signals that fall out of the range of typical signal acquisitions can be compared with error signals of a structurally identical accelerator to help predict an error situation earlier during the prognosis.

It is advantageous to have at least one digitized characterizing signal, outcome of evaluation, reference signal and/or at least one further system-specific item of information present in the data processing system. The information is displayed on one or more screens, connected by a data connection to the data processing system after a program is called up. One or more service technicians involved can access not only the characterizing signals but also outcomes of evaluation or reference signals on which the evaluation is based or further system-specific information. The screen used for the display can be associated directly with the data processing system, or it may be a screen of a workstation of a technician. It is possible for a plurality of service technicians, working on an accelerator system, an association of systems, or in a separate service system to be able to access the same data. Thus, the technicians can work together as needed during error analysis or maintenance. The workstations with the screens, in the form of monitors, displays, or the like, can have computer systems that are a part of a network connected to the data processing system in which the signals and so forth are archived.

At least one characterizing signal and/or outcomes of evaluation can be displayed on a mobile and/or spatially remote screen from the accelerator system. The display on a mobile screen, optionally conceived for use in the accelerator system, makes error analysis possible in nearly real time. Analysis is possible even in the event that the service technician is not in the data processing room at that moment. A mobile screen of this kind can be the screen of a notebook or of a smaller device adapted as needed for use in the accelerator system. For example, a handheld device or device with similar dimensions may be adapted to the accelerator system. The display on remote screens makes it easier to consult external experts, for example, the manufacturer. Communication with relatively large accelerator systems and analysis for a well-founded error assessment and maintenance, are possible because of this site-related integration.

The display can be done numerically, graphically and/or as a function of the operating state of the accelerator. For example, numerical values identifying the amplitude or width of a signal or the like can be output while the signal is displayed in the form of a graphic. Outcomes of evaluation can also be displayed numerically or prepared in graphic form, to make it easier for a technician or user to pick up the results intuitively. The display of the operating state of the accelerator can also depend for instance on the display initially, during normal function, of a character or symbol for unimpaired operation. For detailed data, certain call-ups are actuated in a program. It is also conceivable for only data pertaining to operation that is not up to standard to be displayed, while data for normal operation is accessed separately.

The at least one characterizing signal can be a wave signal or a waveform. In medical accelerators, depending on the principle employed, electron beams, photon beams or particle beams are transmitted, normally in pulsating form, characterized by the energy or intensity of a particular pulse or spill. The signals that can be picked up at different components of the accelerator and that characterize the operating state are generally wave signals or waveforms. A wave signal or waveform is understood here to mean any signal that does not involve a direct current signal, such as a pulse signal. However, still other signals can be acquired, as long as they are characteristic of the operating state.

For example, characterizing signals that can be used are signals of a target, an accelerator chamber, a klystron, of a radiation source and/or of the generated radiation. In typical linear accelerators, for example, electrons are introduced by a radiation source, in this case an electron gun, into a waveguide. Energy is also introduced into the waveguide to accelerate the electrons. This involves high-frequency waves from a high-frequency source. The amount of energy introduced must be adapted to the quantity of electrons introduced, while the frequency of the high-frequency radiation must correspond to the geometry of the waveguide or given cell dimensions. The high-frequency radiation is created by charging a capacitor battery for a few milliseconds and releasing this energy f in a high-energy pulse, in order to amplify or generate high-frequency waves, for example in klystron tubes or magnetron tubes.

All these events are associated with wave signals and waveforms that characterize the operation of the accelerator. Alterations in the amplitude, width, or an envelope curve, for example, of signals that are associated with these components can indicate functional problems of the accelerator. Waveforms are arbitrary signals, to be observed on an oscilloscope, that are not direct current signals in the narrower sense.

As characterizing signals, a beam current, dosage pulse, the voltage and/or the current of the radiation source, the injection current, a generated radiation pulse, the reflected generated radiation, and/or the signals characterizing the beam generation, in particular current and/or voltage and/or pulses, can be acquired. A beam current is generated when the electrons strike the target. The area of this signal, or in other words the product of its width and amplitude is proportional to the dose that is associated with a single radiation pulse. The amplitude alone is a measure of the intensity. A lesser amplitude is an indication that not enough electrons have reached the target. An unconventional width can indicate an incorrect synchronization. An alternation in the envelope curve, for example, when a rounded signal instead of an angular signal is obtained, is an indication of the wrong amount of high-frequency energy. A change in the impedance of the klystron or the ratio between the voltage and the current of the klystron can also indicate that replacement may soon be necessary. It is advantageous to be able to make a replacement without first having to wait for failures in operation, for example, interruptions in operation because of interlocks. Similarly, the injection current is a measure for the assessment of the quality or capability of the injector to function. A missing signal for the reflected high-frequency wave is an indication that high-frequency radiation has not been generated, or possibly that high frequency radiation is not being measured. A change in the form is an indication of a tuning problem on the part of the automatic frequency controller. The area of the dosage pulse signal indicates the dose per pulse, while the amplitude of the signal depends on the quantity of electrons of a linear accelerator that reach the dosage chamber. For example, a drift in amplitude is an indication of a drift on the part of the injector.

System-specific information of the energy supply, the temperature monitoring, and/or a water flow sensor can be acquired and/or utilized for an evaluation. This information also plays a role in the troubleshooting or for status-based maintenance. However, in comparison to the signals that characterize the operation and in view of the accelerator operation, this signal represents static information that may not be sufficient by itself to provide a picture of the entire system during the ongoing phase. It is also advantageous for this additional system-specific information to be acquired and included in an evaluation because in the event of the wrong temperature setting, a problem with the energy supply, or the cooling, impairment in operation and thus in the signals characterizing the operation are unavoidable. The additional acquisition of basic data and the evaluation of this data, as initial basic check can be performed. Connecting an external oscilloscope to the accelerator system can also be done. Real-time observation can be achieved with an oscilloscope. With an oscilloscope, an expanded data acquisition or optionally a signal acquisition with higher time resolution can be achieved in order to expand the function monitoring with signal acquisition. In the event of an error situation detected in the evaluation in the data processing system, an error report can be generated and/or the accelerator operation can be adapted, and in particular interrupted. In this case, not only is an outcome of evaluation generated and optionally deposited, but the user of the accelerator system also explicitly receives an error report. The error report can be visual and/or acoustic. For example, the generation of a warning sound and a blinking, highlighted, on-screen text report that indicates the error can be used. This kind of error report that is intended to direct the attention of a service technician to observe the incoming signals from the accelerator system should be output in such a way that the attention of a user is diverted from an activity he would otherwise be performing. Optionally, the accelerator operation can be interrupted after the intervention of a technician.

Further security is provided via the data processing system that goes beyond the possibility of blocking provided in previous accelerator systems. The accelerator operation can also optionally be altered as a function of rule-based specifications or corresponding inputs by a technician in a program, for example, by adapting the energy supply and the like.

The data deposition can be effected by a database of the data processing system. In such a database, the acquired signals, the outcomes of evaluation obtained, and further system-specific information and reference signals can be deposited systematically. The signals can be deposited in a way that they can easily be found using search masks. Generally, databases have easily adjusted or regularly employed ordering and deleting routines and instructions that can be adapted to the problem of function monitoring of the accelerator system.

The characterizing signal and/or at least one trigger signal of the accelerator can be acquired by a device for signal acquisition. More specifically, this acquisition is performed by a device which forms part of the data processing system and which digitizes the signal and/or exchanges data with a program of the data processing system. More specifically, for example, the signals are digitized signals, trigger signals, and/or further acquisition specifications. The device for signal acquisition converts the analog signals of the accelerator or accelerators into digital signals that are then stored in memory and optionally evaluated by the data processing system. The device for signal acquisition can be logically and spatially separate from the data processing system, but expediently forms part of the data processing system. Data, such as digitized signals, trigger signals, and other acquisition specifications, can be exchanged between the device for signal acquisition and a program that controls the acquisition, display and evaluation of data. For example, instructions that a signal acquisition is to be made every ten treatments can be made via inputs in a program and then sent onward from the program to the device for signal acquisition. The device for signal acquisition in turn receives the internal trigger signals and other information from the accelerator. Thus, a function of this internal accelerator information, a signal acquisition and ensuing digitization of the signal are done in accordance with the predetermined trigger signal or the acquisition specification of the program.

A medical accelerator may use, for example, a linear accelerator and/or a cyclic accelerator, in particular a synchrotron and/or a cyclotron. Depending on the type of accelerator, different kinds of signals should be acquired as needed. Function monitoring as described enables any accelerator system because a plurality of signals are automatically detected, and signal acquisition is also possible from various individual accelerators, depending on the application from further devices that are to be found in an accelerator system.

DRAWINGS

Further advantages, characteristics and details will become apparent from the ensuing exemplary embodiments and from the drawings. In the drawings.

DESCRIPTION

Figure 1:
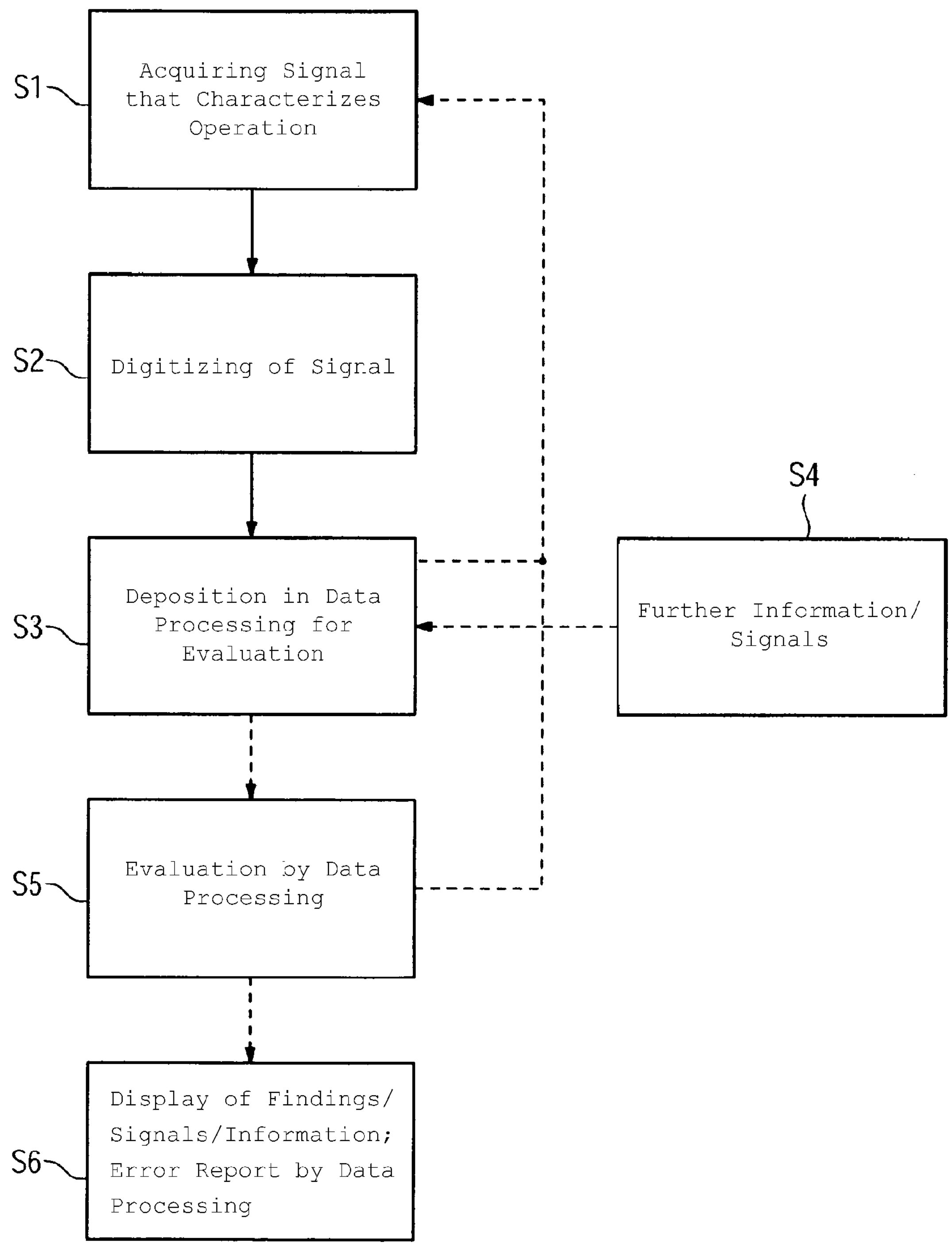
FIG. 1 is a flow chart of a method for function monitoring of accelerator systems.

FIG. 1 shows a flow chart of a method for function monitoring in an accelerator system. First, in an act S1, a signal that characterizes the operation of an accelerator of the accelerator system is acquired. This signal is then digitized in act S2, using a suitable device. After the digitization, the digital signal is deposited in act S3 in a data processing system for evaluation. The evaluation can be done as needed by a service technician, or alternatively can be performed by the data processing system, as shown in act S5. The evaluation by the data processing system, which is shown in act S5 is optional, as represented by the arrow drawn in dashed lines. It is accomplished by a suitable program.

Other characterizing signals and other kinds of signals as well as other system-specific information, as shown in act S4, are also deposited in the data processing system and kept in reserve for later evaluation. It is appropriate for as many signals as possible of an accelerator that characterize the operation to be acquired. Acquiring a large array of signals enables the most comprehensive possible evaluation, especially in the event that the evaluation is done with a certain time lag, meaning that missing signals can no longer be retroactively picked up.

Further system-specific information, such as indications from a water flow sensor for the cooling or the like, are also picked up in order to archive basic data for the operation of the accelerator system. The deposition in the data processing system is done for a predetermined time. This time period can be changed by a user based on a desired "life span" of each signal, defined in a database of the data processing system. The "life span" is varied by the number of total data collected and of the newly acquired data or by the elimination of an existing problem.

The further signals that are delivered to the data processing system in act S4 may also be signals of different accelerators of the accelerator system. For example, typical accelerator systems in medical facilities that specialize in oncology are on the order of magnitude of up to ten different or structurally identical accelerators. The deposition in the data processing system in act S3 and the evaluation by the data processing system in act S5 can be followed by a new signal acquisition. This allows the characterizing signal to be acquired for different ongoing phases of the accelerator or at different times or time stamps or at certain intervals.

The function monitoring is done in a chronologically integrated way because signals in the event of errors or in accordance with corresponding acquisition specifications are acquired and archived multiple times. A local integration is also done by picking up a plurality of signals and similar signals from different accelerators and displaying them in the context of act S6 on different screens or at different workstations. A display may be made of outcomes of evaluation, further information, and error reports that are generated by the data processing system.

Function monitoring, in the sense of data acquisition and maintenance that is to be performed as well as troubleshooting, is done automatically or without the intervention of a user. Monitoring can be done continuously, and at the same time local limits are overcome by a technician at a distance or a plurality of technicians working at different workstations. The technicians may be equipped with mobile screens and can act together in monitoring and later checking the function of the accelerator. The function monitoring is no longer bound to the actual occurrence of an error or certain maintenance intervals. It is possible to document operation comprehensively and to detect errors in the context of a prognosis before a failure of the accelerator actually occurs. Consequent damage can be avoided, and costs that occur from an unplanned failure in operation can be avoided.

Figure 2:
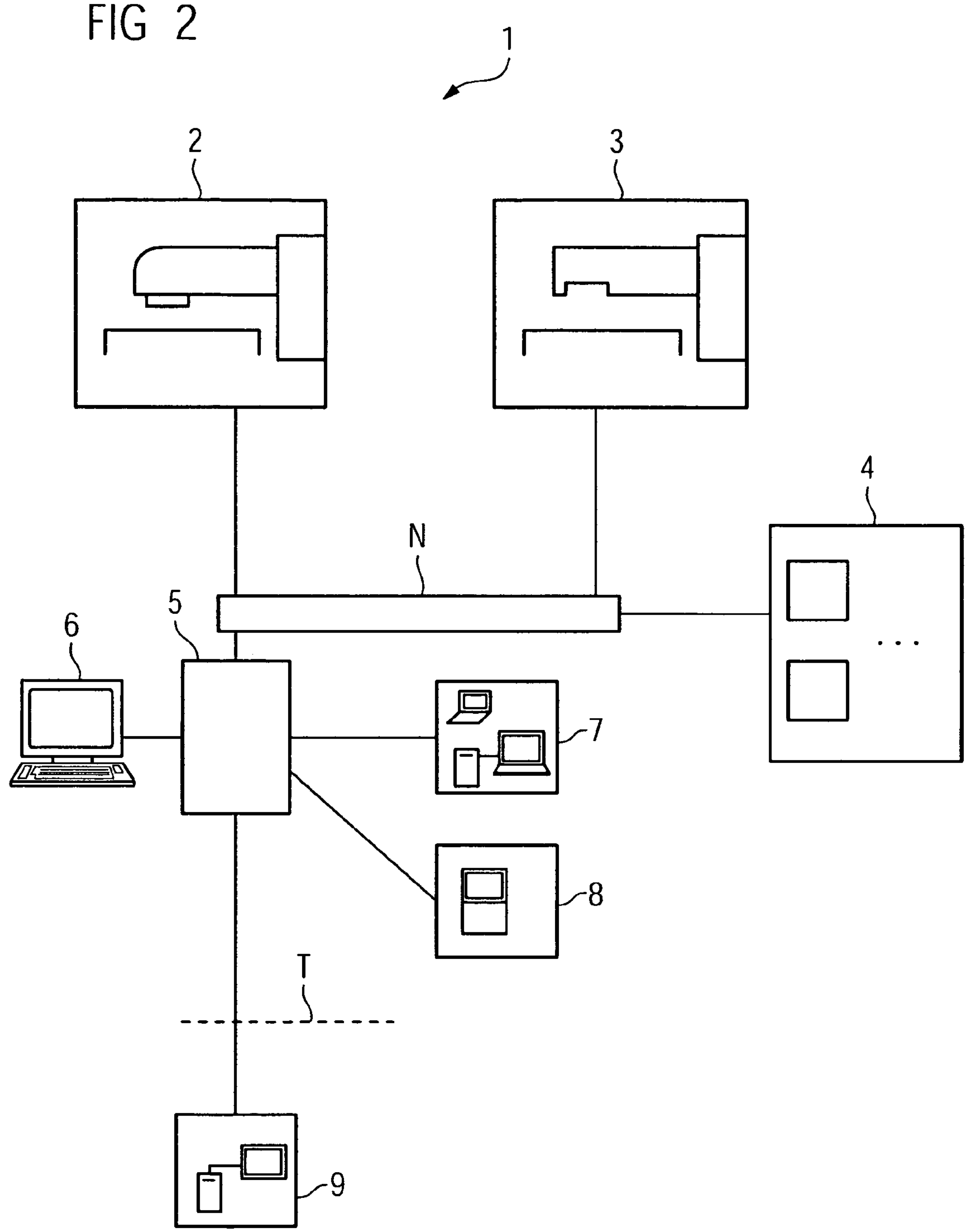
FIG. 2 shows a medical accelerator system according to one embodiment.

FIG. 2 shows a medical accelerator system 1. The accelerator system 1 is used in radiation therapy of patients and has a plurality of medical accelerators 2, 3, which are linear accelerators, as well as other accelerators 4, which may also be linear accelerators or cyclic accelerators. The accelerators 2, 3, 4 of the accelerator system 1 are connected via a network N to a data processing system 5. A device for signal acquisition is integrated into the data processing system 5. The acquisition of signals that characterize the operation of the particular accelerator 2, 3, 4 is accomplished. These signals are deposited for subsequent computer-supported evaluation in the data processing system 5 in digital form after digitizing has been performed. In the data processing system 5, an evaluation of the characterizing signals is done based on predetermined rules or existing reference signals. Other information obtained from the accelerators 2, 3, 4 via the network N or information that characterizes the accelerator system 1 in some other way is taken into account.

Screen 6 is a display used in conjunction with data processing systems. The digitized characterizing signal is displayed along with outcomes of evaluation and together with reference signals and other system-specific information on the screen 6. This is done after a user, generally a technician of the accelerator system 1, has started a corresponding program that is capable of running essentially uninterrupted for data acquisition in continuous form. The screen 6 has an input device, with which certain acquisition specifications can be specified by the user, and thus specifications on the part of the data processing system 5 can be expanded or adapted. In conjunction with internal trigger signals of the accelerators 2, 3, 4 and trigger signals that are specified for the signal acquisition, a signal acquisition and archiving in the data processing system 5 are performed at certain times or as a function of the operating states of the accelerators 2, 3, 4.

The signals and outcomes of evaluation and the like are displayed on further screens 7, 8 and 9. The screens 7 are screens at workstations of further service technicians of the accelerator system 1, some of which have their own associated computer devices that are connected to the data processing system 5 via the network N. The screen 9 is located at a distance from the data processing system 5 as indicated by the dividing line T. The signals and outcomes of evaluation can be displaced to an external expert, working at screen 9, who can thereupon, either directly by means of a program or by way of communicating with service technicians on-site, causing adaptation to be made in the operation of the accelerators 2, 3, 4 if a malfunction is found or an optimization is to be performed. Error reports are also optionally generated at the screens 6 through 9. An error report can be generated when characterizing signals are acquired that call for rapid intervention or even an interruption in operation. Error reports can be displayed to a service technician on a screen 8 that is mobile. The service technician can be located either at an arbitrary site accessible via data connections inside the accelerator system 1 or even at a distance from the accelerator system 1. The service technician is optionally informed of these signals or error reports with a warning that is tripped optically, acoustically, or by a vibration alarm.

Figures 3A, 3B, 3C:
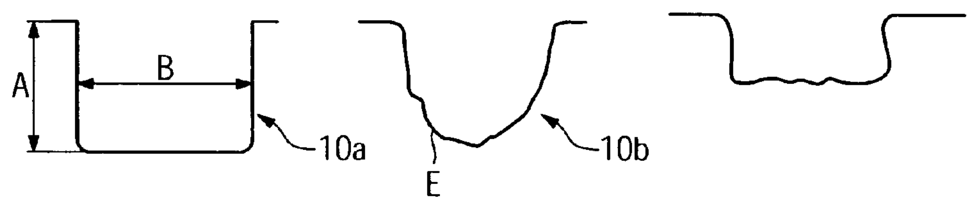
FIGS. 3A-3C show example beam currents, picked up in a method of the invention, at a target.

FIGS. 3A through 3C show beam currents 10*a* and 10*b* acquired in the function monitoring method. The beam current 10*a* in FIG. 3A can be associated with error-free operation of the accelerator. A substantially square pulse with a predetermined amplitude A and a width B is displayed, for instance within the range of a few microseconds. If an error occurs, as shown in FIG. 3B, in which the beam current 10*b* has a deviant envelope curve E with a rounding of the signal, an error exists in the high-frequency radiation. This is recognized through an evaluation by the technician or by the data processing system in a comparison with a reference signal, as shown in FIG. 3A, so that a targeted elimination of the problem is possible. Other errors that can occur in accelerator operation also involve characteristic changes in the form, amplitude, width, and in the envelope curve. The outcome of evaluation is displayed on a screen and archived in the data processing system.

Figure 4:
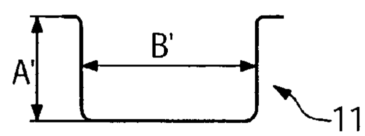
FIG. 4A shows an example injection current, picked up as a signal that qualitatively characterizes the operation of a linear accelerator.

FIG. 4 shows an injection current 11 acquired as a signal characterizing the operation of a linear accelerator. The injection current 11 is also a substantially square signal as long as the operation is proceeding without error. Once again, there are certain specifications and optimal settings for the amplitude A' and for the signal width B'. For example, the signal width is in the range of a few microseconds, in this case 5 μs, while a typical value for the amplitude A' is 1 ampere. A decrease in the amplitude A' is an indication of too few injected electrons, while an increase in amplitude indicates a high number of injected electrons. Unstable or drifting signals can also be picked up that indicate a problem with the electron gun or a problem in the tuning and voltage adaptation, while a peak signals a disruptive discharge.

Figure 5A:
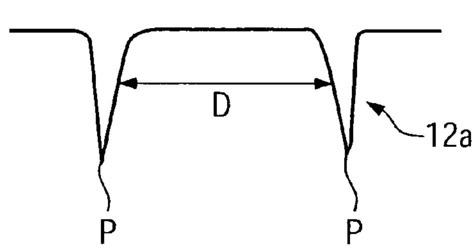
FIGS. 5A and 5B are exemplary illustrations of the reflected high-frequency radiation.
Figure 5B:
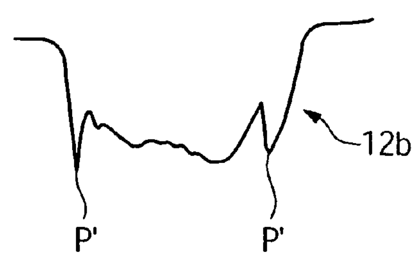

In FIGS. 5A and 5B, illustrations are shown of the reflected high-frequency radiation. The reflected radiation 12*a* of FIG. 5A shows standard operation with two peaks P with form and amplitude that are very similar. The spacing D between the two peaks is in the range of specifications. For example, the spacing is at approximately 3 μs. In FIG. 5B, a reflected radiation 12*b* is shown that is an indication of an error in operation. These peaks P' are not very pronounced, and the signal in the intermediate region no longer returns to the initial value. This is an indication of a problem in the setting of the high-frequency radiation by the frequency controller. A problem in the setting of the high-frequency radiation by the frequency controller can be recognized immediately when signal acquisition is done continuously. An evaluation by the data processing system identifies the problem through a comparison with a reference signal as in FIG. 5A.

Figure 6A:
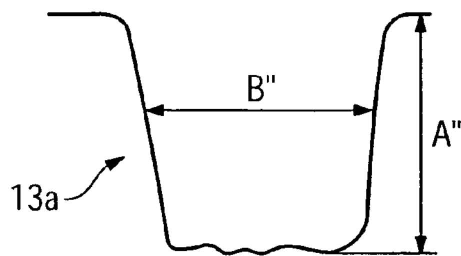
FIGS. 6A and 6B show example klystron currents picked up as characterizing signals.
Figure 6B:
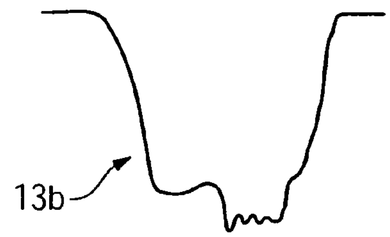

In FIGS. 6A and 6B, klystron currents acquired as characterizing signals are shown. The klystron current 13*a* of FIG. 6A is a wave signal with amplitude A" of a few tens of amperes, and the width B" is a few microseconds long. The klystron current, as shown in FIG. 6A, corresponds to a good operating state without errors. By comparison, the klystron current 13*b* of FIG. 6B within the wave pulse shows a greater amplitude variation that is an indication of the occurrence of an electric arc. In accordance with this associated error, an error report is generated for the user.

Figure 7:
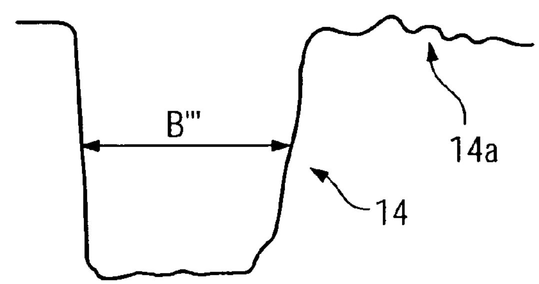
FIG. 7 shows an example klystron voltage picked up as a characterizing signal.

In FIG. 7, a klystron voltage 14, acquired as a characterizing signal, is shown with a trailing region that has small residual waves 14*a*. The width of the signal is again set to an optimal value B'''. In the event of an error, the signal width B''' changes, the wave residues 14*a* are overly pronounced, or peaks occur in the signal direction that indicate the occurrence of an electric arc. Pronounced wave residues 14*a* indicate a maladaptation between the klystron tube and the modulator.

Figure 8:
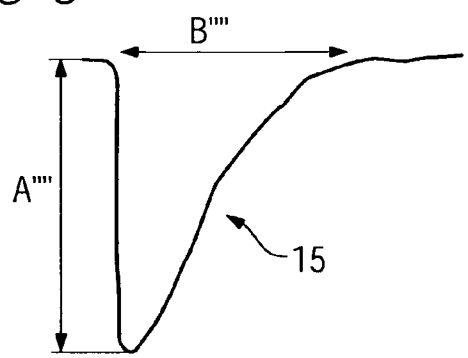
FIG. 8 shows an example dosage pulse of an ionization chamber.

FIG. 8 shows a dosage pulse of an ionization chamber. The dosage pulse 15 is an indication of error-free operation, with a signal width B'''' of approximately 200 μs and an amplitude A'''' of approximately 6 V. In the event of an error, dosage pulses with lesser amplitudes result if too few electrons have been injected, the high-frequency radiation generated is unstable, or the amount of radiation is not correctly set. At the beginning, an increase in the pulse can also occur that is an indication of back heating of the cathode of the electron gun.

Figure 9:
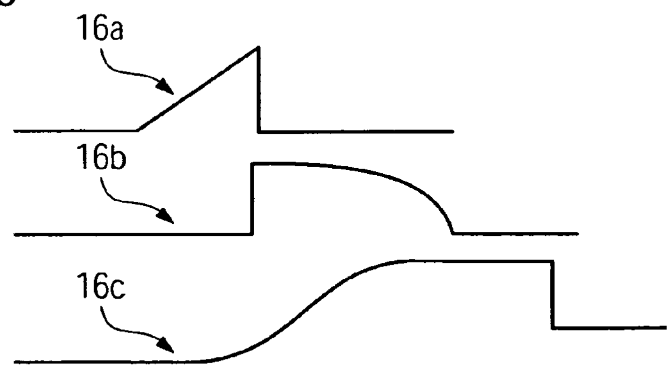
FIG. 9 shows example waveforms, picked up as characterizing signals, for currents and voltages of a modulator of an accelerator.

FIG. 9 shows current and voltage waves 16*a* through 16*c* of a modulator. The waves occur in rated operation of a linear accelerator. The signals 16*a* and 16*b* are current signals and the signal 16*c* represents the voltage. These signals 16*a* through 16*c* characterize the production of the high-frequency radiation and in the event of an error, such as incorrect triggering, the individual signals 16*a* through 16*c* experience characteristic changes in their form.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A method for function monitoring in medical accelerator systems with at least one signal characterizing an operation of at least one medical accelerator, the method comprising:

digitizing the at least one signal;

depositing in digitized form the at least one signal in a data processing system;

holding the at least one signal at least until evaluation of the accelerator system occurs, and evaluating, by the data processing system, the width, envelope curve, form, or any combination thereof of the at least one signal, wherein evaluating comprises making a prognosis in terms of an operating state of the at least one medical accelerator.

2. The method according to claim 1, further comprising:

evaluating the at least one signal characterizing the operation in the data processing system, the evaluating being as a function of rules, a function of a comparison, or the combination thereof, and wherein an acquired signal, predetermined reference signal, or the combination thereof is used during the evaluating of the at least one signal.

3. The method according to claim 2, wherein the prognosis is made in terms of the operating state of the at least one medical accelerator system.

4. The method according to claim 1, further comprising:

depositing the outcome of the evaluation in the data processing system for a predetermined length of time, a length of time that can be defined by a user, or the combination thereof.

5. The method according to claim 1, further comprising:

depositing, the at least one characterizing signal in the data processing system for a predetermined length of time, a length of time that can be defined by a user, or the combination thereof.

6. The method according to claim 1, further comprising:

acquiring the at least one signal as a function of acquisition specifications, wherein the at least one signal is acquired continuously, at certain times, at certain time intervals, as a function of at least one trigger signal, multiple times, or any combination thereof.

7. The method according to claim 1, further comprising:

acquiring the at least one signal as a plurality of different characterizing signals.

8. The method according to claim 1, further comprising:

acquiring the at least one signal as a plurality of signals from a respective plurality of accelerators.

9. The method according to claim 8, wherein each of the plurality of accelerators is structurally identical, similar, or the combination thereof to one another.

10. The method according to claim 1, further comprising:

displaying the at least one digitized signal, an outcome of evaluation, a reference signal, at least one system-specific item of information present in the data processing system, or any combination thereof on one or more screens, and connecting the screens by a data connection to the data processing system after a program is called.

11. The method according to claim 10, further comprising:

acquiring, the at least one system-specific item of information, and wherein the system-specific item is the energy supply, temperature monitoring, to a water flow sensor, or the combination thereof.

12. The method according to claim 1, further comprising:

displaying the at least one signal, an outcome of evaluation, or the combination thereof on a mobile screen, spatially remote screen from the at least one medical accelerator system, or the combination thereof.

13. The method according to claim 12, wherein the display is numerical, graphical, a function of the operating state of the at least one medical accelerator, or any combination thereof.

14. The method according to claim 1, wherein digitizing comprises digitizing the at least one characterizing signal as a wave signal.

15. The method according to claim 1, further comprising:

acquiring the at least one signal as a signal of a target, an accelerator chamber, a klystron, a radiation source, the generated radiation, or any combination thereof.

16. The method according to claim 1, further comprising:

acquiring the at least one signal as a beam current, dosage pulse, the voltage, the current of the radiation source, the injection current, a generated radiation pulse, the reflected generated radiation, the signals characterizing the beam generation, or any combination thereof are acquired, and wherein signals characterizing the beam generation are current, voltage, pulses, or the combination thereof.

17. The method according to claim 1, further comprising:

detecting an error situation with an evaluation by the data processing system; and generating an error report, interrupting the accelerator operation, or the combination thereof.

18. The method according to claim 1, wherein the data deposition is effected by a database of the data processing system.

19. The method according to claim 1, further comprising:

acquiring the at least one signal, at least one trigger signal, or the combination thereof of the accelerator with a device for signal acquisition, wherein the device forms part of the data processing system and digitizes the signal, exchanges data, or the combination thereof with a program of the data processing system

20. The method according to claim 1, wherein the at least one medical accelerator system comprises a medical accelerator, a linear accelerator, a cyclic accelerator, or the combination thereof, and wherein the medical accelerator is a synchrotron, a cyclotron, or the combination thereof.

21. The method according to claim 1, further comprising:

evaluating the at least one signal characterizing the operation in the data processing system as a function of predetermined rules, as a function of a comparison, or the combination thereof with at least one acquired signal, predetermined reference signal, or the combination thereof.

22. The method according to claim 1, wherein the operating state of the accelerator comprises an expected service life for error-free operation.

23. A medical accelerator system comprising:

a device operable to digitize at least one signal characterizing an operation of the medical accelerator system;

a data storage operable to receive and hold, in digitized form, the at least one signal; and a data processing system operable to evaluate the width, envelope curve, form, or any combination thereof of the at least one signal from the data storage, wherein the data processing system makes a prognosis in terms of an operating state of the accelerator.

* * * * *